United States Patent [19]

Braetsch et al.

[11] Patent Number: 4,523,911
[45] Date of Patent: Jun. 18, 1985

[54] FOOT-ACTUATED CONTROL ARRANGMENT PARTICULARLY FOR DENTAL ARRANGMENT

[75] Inventors: Hartmut Braetsch, Schemmerhofen; Karl Herter, Warthausen, both of Fed. Rep. of Germany

[73] Assignee: Kaltenbach & Voight GmbH & Co., Biberach, Fed. Rep. of Germany

[21] Appl. No.: 571,507

[22] Filed: Jan. 17, 1984

[30] Foreign Application Priority Data

Jan. 26, 1983 [DE] Fed. Rep. of Germany ....... 3302558

[51] Int. Cl.³ .............................................. A61C 1/02
[52] U.S. Cl. ................. 433/101; 200/153 C; 251/295
[58] Field of Search .................... 433/101; 200/153 C; 251/295; 318/551

[56] References Cited

U.S. PATENT DOCUMENTS

| | | | |
|---|---|---|---|
| 804,595 | 11/1905 | Garhart | 200/153 C |
| 3,359,638 | 12/1967 | Maurer et al. | 433/101 |
| 3,411,209 | 11/1968 | Stemler et al. | 433/101 |
| 3,476,153 | 11/1969 | Roland | 433/101 |
| 3,886,660 | 6/1975 | Thornton, Jr. et al. | 433/101 |

*Primary Examiner*—John J. Wilson
*Attorney, Agent, or Firm*—Scully, Scott, Murphy and Presser

[57] ABSTRACT

A foot-actuated control arrangement, in particular for dental apparatuses, including an actuating element acting on a switch or control element, and which is equipped with a treadle. The actuating element is displaceable towards both sides from an initial position in one plane, is displaceable along a pivoted path about a stationary position, and can be restrained through at least one setting or control element in the mentioned initial position along the pivoted path and, subsequent to a displacement from this position, can be automatically returned thereto.

9 Claims, 7 Drawing Figures

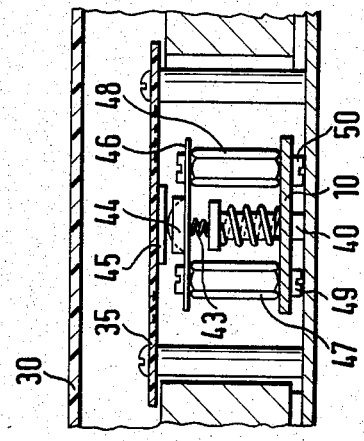
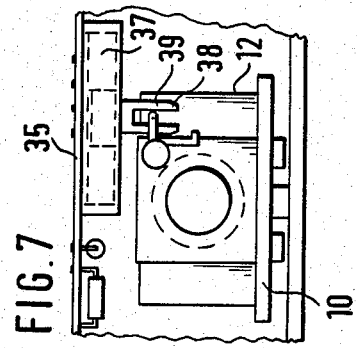
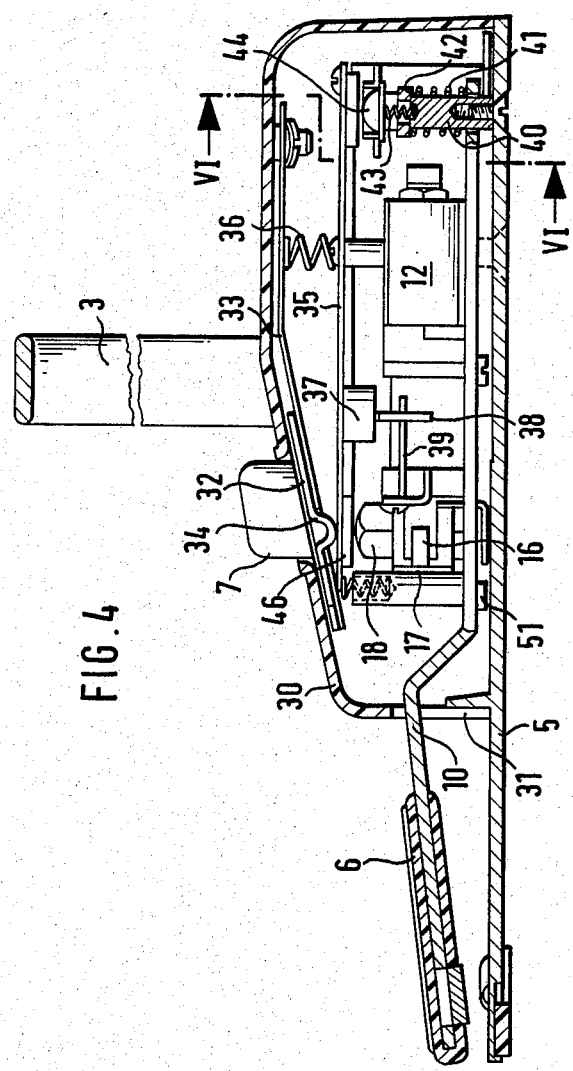

FOOT-ACTUATED CONTROL ARRANGMENT PARTICULARLY FOR DENTAL ARRANGMENT

BACKGROUND OF THE INVENTION

1. Field of the Invention

The present invention relates to a foot-actuated control arrangement, in particular for dental apparatuses, including an actuating element acting on a switch or control element, and which is equipped with a treadle. The actuating element is displaceable towards both sides from an initial position in one plane, being displaceable along a pivoted path about a stationary position, and can be restrained through at least one setting or control element in the mentioned initial position along the pivoted path and, subsequent to a displacement from this position, can be automatically returned thereto.

2. Discussion of the Prior Art

A foot-actuated control arrangement of the above-described type has already become known from German Pat. No. 641,306. In this known foot-actuated control arrangement, the actuating element which is constructed as a foot-actuated lever is restrained in its defined initial position through the aid of contact springs. In addition to the applicable foot there is provided a further foot pedal which is drawn in a similar manner into a definite initial position by means of a separate spring. Consequently, these foot levers or actuating elements cannot be restrained in every suitable fixed position along their respective pivoting paths.

Furthermore, a foot pedal starter is known, which includes a latching device which can be extended by means of a push rod; as is disclosed in German Pat. No. 683,037. Hereby, a foot lever is rigidly connected with a latching path which serves for stepped regulating, and wherein the latch element is constructed as a resilient catch member which is fastened on a support base plate. Through the intermediary of a separate spring-loaded actuating element, in the known foot pedal starter the latching member lock which is provided can be rendered either operative or inoperative. However, in every instance, the foot lever is restrained in a definite initial or median position through the action of a resilient resetting device, into which it is automatically returned after its displacement. This known foot pedal starter is also subject to the disadvantage which has been described in connection with the previously considered foot-actuated control arrangement.

Finally, from German Pat. No. 22 31 265 there has also become known a foot-actuated control arrangement of the above-described type, in which the actuating element is restrained in two fixed or stationary positions, which form the corners of a horizontally oriented triangle, whereby the rotation of the actuating element from its stationary position presently effects a corresponding rotational movement about only one stationary position of the two stationary or fixed positions. Also in this known foot-actuated control arrangement, the actuating element is automatically returned into its initial position subsequent to each effected setting.

It has been ascertained that, in many instances, it is inadequate to provide a foot-actuated control arrangement whose actuating element, subsequent to each actuation, is again automatically returned to an initial position. Occasionally, it is necessary or desired that the actuating element of a foot-actuated control arrangement can be maintained in each set position subsequent to the effected setting without causing an automatic return into an initial position. In order to meet that type of requirement, predicated on the above considered known arrangements, there must also be provided separate foot-operated control devices. Inasmuch as for the implementation of the two functions there must be provided practically always two separate foot-actuated control devices, this requires significant constructional demands. In addition thereto, also disadvantageous is the necessarily large spatial requirement, and the danger of possible confusion among the currently provided foot-actuated control devices.

SUMMARY OF THE INVENTION

Accordingly, it is a primary object of the present invention to describe a mode in which a foot-actuated control arrangement of the above-described type can be modified or improved whereby its actuating element is not only automatically returnable into a defined initial position, but can also selectively remain in every suitable set position.

The object pursuant to the present invention is achieved in a foot-actuated control arrangement of the above-mentioned type in that the respective control element is an electromagnetic and/or pneumatic, or hydraulically controllable setting or control element which, responsive to the supply or disappearance of a separate control signal can be placed from its condition for automatic return into a condition which will not provide for returning thereof, and in which the actuating element is adapted to remain in every possible set position along its pivoting path of movement.

The invention possesses the inherent advantage in the creation of a foot-actuated control arrangement which is employable not only as a pivot lever-foot actuated control arrangement with automatic return of its actuating element into an initial position, but that this can also remain as a foot treadle-like control arrangement in which the actuator element can remain in every assumed setting position along the pivoting path of movement without being automatically displaced therefrom. Moreover, the invention provides the advantage in that no mechanical elements are required, but the control element is remotely-controllable whereby, with the aid of remote control signals, the required switching procedures can be effected through for the foot-actuated control arrangement.

Preferably, the setting or control element is displaceable about fixed location in a direction which extends transverse to the mentioned plane; wherein the setting element, during the course of its displacement about this fixed location, allows for the positioning or actuation of a control and/or switch element. This provides the advantage that the extent of applicability of the control arrangement pursuant to the invention is increased still further. The displaceability of the control element in a direction which extends transverse to the mentioned direction which extends in one plane is hereby possible in every set position of the control element.

When there is employed an actuating element having a contact element which supports itself along a guide, then the setting or control is preferably formed of or encompasses this contact element. This provides the advantage of an especially simple structure for the foot-actuated control arrangement.

Preferably, the contact element incorporates hereby a tread element which is located opposite a V-shaped guide track, which has its separating point facing away from the tread element, and which is fixed at both of its ends relative to the support position of the actuating element. Obtained herewith is the advantage of a particularly simply constructed arrangement for the determination of the initial position into which the actuating element, as needed, can be automatically returned. In addition thereto, through selection in the shape of the V-shaped guide, there can be effected a correlation with different characteristics relative to the return setting of the actuating element, with regard to the control of auxiliary devices which are controlled by means of the actuated setting element.

Preferably, the above-mentioned tread element is provided with a roller at the end which faces towards the V-shaped guide. This imparts the advantage of a particularly simple construction to the arrangement.

A particularly compact construction is obtained when the control element contains a hydraulically or pneumatically-actuatable piston, which is connected with the actuating element.

The opening or closing of the hydraulic or pneumatic circuit of the above-mentioned piston is preferably controllable by means of an electromagnet. This provides the advantage of a particularly simple control of the hydraulically or pneumatically-actuatable piston.

However, it is also possible to merely employ an electromagnetic arrangement as the setting element, such as a lifting magnet or solenoid, which is connected, for example, with the actuating element. Obtained hereby is the advantage that the control element can be constructed particularly simple.

Finally, it is however also possible that the control element be constructed as a linear motor which is connected with the actuating element. This provides the advantage that no movable component are required in order to form the actuating element.

BRIEF DESCRIPTION OF THE DRAWINGS

Reference may now be had to the following detailed descriptions of exemplary embodiments of the invention, taken in conjunction with the accompanying drawings; in which:

FIG. 4 illustrates a side elevational view of the foot-actuated control arrangement of FIG. 2, shown partially sectioned;

FIG. 5 illustrates the foot-actuated control arrangement of FIG. 4 in another set position;

FIG. 6 illustrates a sectional view taken along lines VI—VI in FIG. 4; and

FIG. 7 illustrates, on an enlarged scale, a detail of the foot-actuated control arrangement shown in FIG. 5.

DETAILED DESCRIPTION

Figure 1:
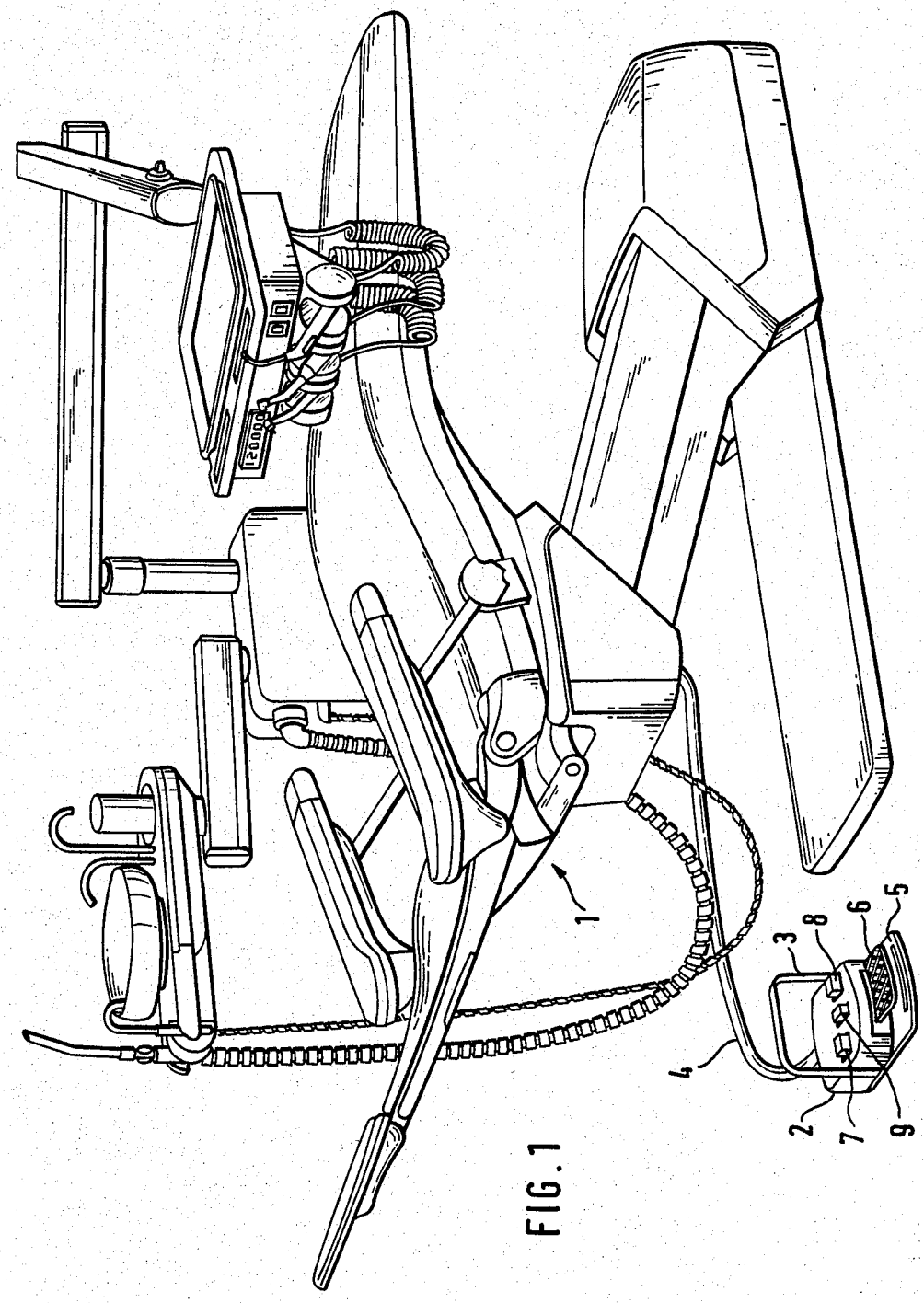
FIG. 1 illustrates a perspective view of a dental treatment location which is equipped with a foot-actuated control arrangement pursuant to the invention.

Illustrated in FIG. 1 is a dental treatment location or facility 1 which is equipped with a foot-actuated control arrangement 2, also designated as foot-actuated starter, which is connected with the dental treatment location 1 through a hose 4. The foot-actuated control arrangement 2 incorporates, as can be ascertained from FIG. 1, a housing which is provided with a carrying sling 3, which is arranged on a base plate 5. A foot pedal 6 projects from the housing, through the displacement of which there can be varied, for example, the rotational speed and, if required, the direction of rotation of a drive motor, and through which an actuating element is pivotable as well as depressable, as is described in further detail hereinbelow. In the present instance, three actuating pushbuttons 7, 8 and 9 are arranged on the housing, of which the pushbutton 7 can serve, for example, for the dispensing of a spray medium, the pushbutton 8 for the dispensing of air blows, and the pushbutton 9 for the control of the left or right-hand drive of a drive motor for the dental treatment instruments of the treatment chair 1.

Figure 2:
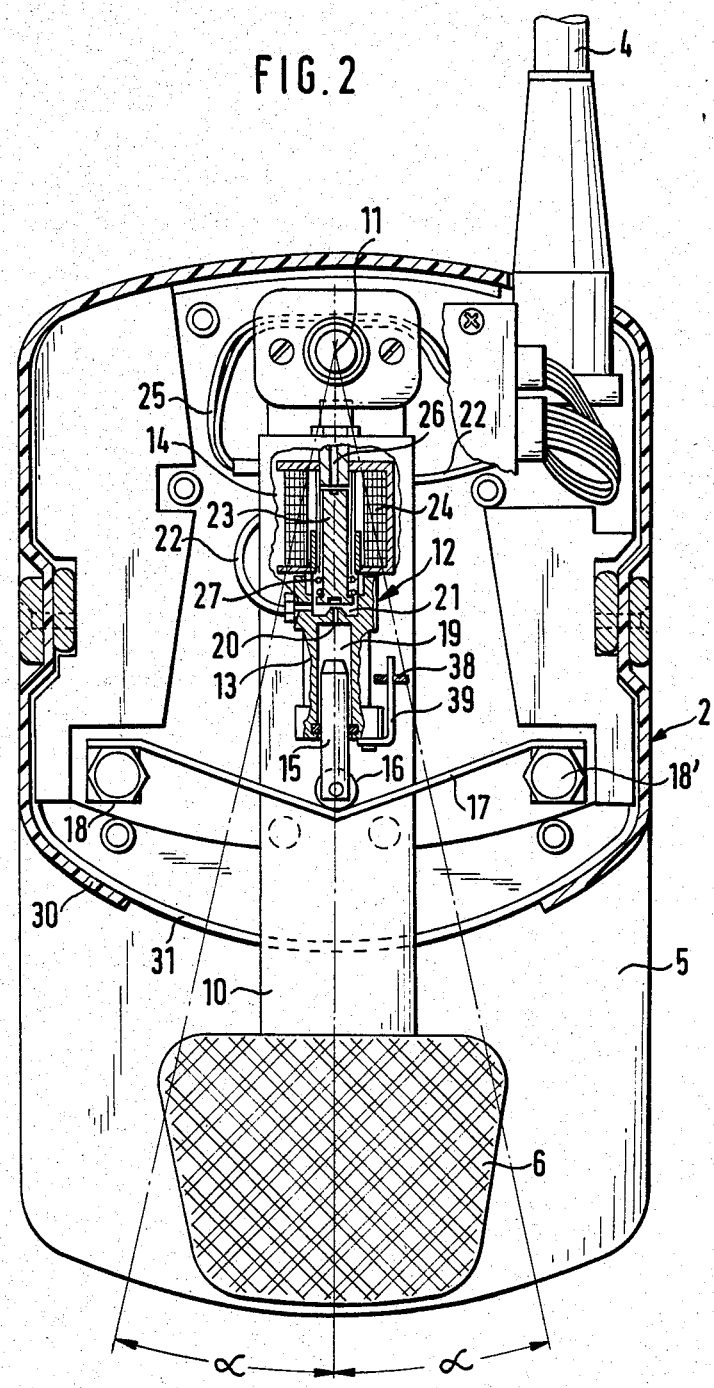
FIG. 2 illustrates a top plan view of one embodiment of the foot-actuated control arrangement pursuant to the invention, shown partially sectioned.

Illustrated in greater detail in FIG. 2 is an embodiment of the foot-actuated control arrangement 2. Supported on the base plate 5 of the illustrated foot-actuated control arrangement 2 is a pivot lever 10 provided with the foot pedal 6 so as to be pivotable about a fixed location 11. The arrangement hereby may be so designed that the pivot lever 10 which forms an actuating element is always displaceable through an angle α from the central or median position.

A control or setting element which is generally identified by reference numeral 12 is arranged on the pivot lever or actuating element 10, which in the present instance is an electro-magnetically controlled pneumatic or hydraulic control element. The control element 12 includes the pneumatic or hydraulic component 13 and an electromagnetic component 14. The pneumatic or hydraulic component 13 includes a pressure piston 15 within a cylinder 19, which is conveyed sealed within the cylinder 19. The cylinder 19 is connected with a chamber 21 by means of a through-opening 20, wherein the chamber is connected by means of a hose 22 with a compressed-air or hydraulic medium source. The hose 22 is contained within the hose 4 and is connected with a compressed-air or hydraulic medium source in the dental treatment location 1 pursuant to FIG. 1.

The opening or, respectively, closing of the above-mentioned opening 20 is effected by means of the armature component 23 of an electromagnet 24 which is arranged in the electromagnetic portion 14 of the control element 12. The electromagnet 24 is connected to a power source through connecting lines 25, which may be contained in the dental treatment location 1 according to FIG. 1. The connecting lines 25 are also contained within the hose 4.

Pursuant to FIG. 2 the armature component 23 in the unexcited condition is pressed by means of a spring 27 against the opening 20 so as to block the latter. Upon the excitation of the electromagnet 24, the armature component 23 is drawn into this electromagnetic 24, whereby the opening 20 represents a connection between the cylinder 19 and the chamber 21. At this point it is noted that, for the unhindered movement of the armature component 23 within the electromagnet 24, there is provided a vent opening 26 in that portion of the applicable arrangement which lies opposite the end of the armature component 23 serving for the opening or closing of the opening 20.

The pressure piston 15 of the pneumatic or hydraulic component 13 of the control element 12 is provided at its forward end with a running element 16 in the form of a roller. This roller 16, in the extended position of the pressure piston 15, lies against a guide track 17 which is constructed in a V-shape, and which, for example, can be a metal guide track which is fixedly connected with base plate 5 at fastening location 18 and 18'.

Also connected with the pneumatic or hydraulic component 13 of the control element 12 is an actuating element 39 which, for example, can have the shape of a wire and which can serve for the control of a switch and/or control element, to which there may belong a setting control element 38. With respect to the setting control element 38, in the present instance this relates as is further explained hereinbelow in greater detail, to the control element of a potentiometer.

The previously described elements, which are arranged on the base plate 5 of the foot-actuated control arrangement, are enclosed by a housing 30 which includes an opening 31 through which there projects outwardly the pivot lever 10 of the actuating element. As a result thereof, as can be ascertained from FIG. 1, the actuating element can be pivoted through the actuation of its foot treadle 6. When one proceeds from the point that the pressure piston 15 of the pneumatic or hydraulic component is extended and remains in an extended position, as can be recognized from FIG. 2, then the actuating element or the pivot lever 10 can be pivoted out of its basic position as shown in FIG. 2 towards either the right or the left, whereby the running roller 16 will constantly contact the V-shaped guide track 17. Thereafter, when the actuating element 10 is released, due to the action of the control element 12 in cooperation with the V-shaped guide track 17 it automatically returns again into its initial or basic position, as is illustrated in FIG. 2. At this point it is noted that the pneumatic or hydraulic circuit is so designed as to facilitate any movement of the pressure piston 15 occasioned within the cylinder 19 which is caused by the pivotal movement of the actuating element 10. Thereby, the applicable foot-actuated control arrangement can be utilized as a pivot lever starter device in a dental treatment location, as is indicated in FIG. 1.

Figure 3:
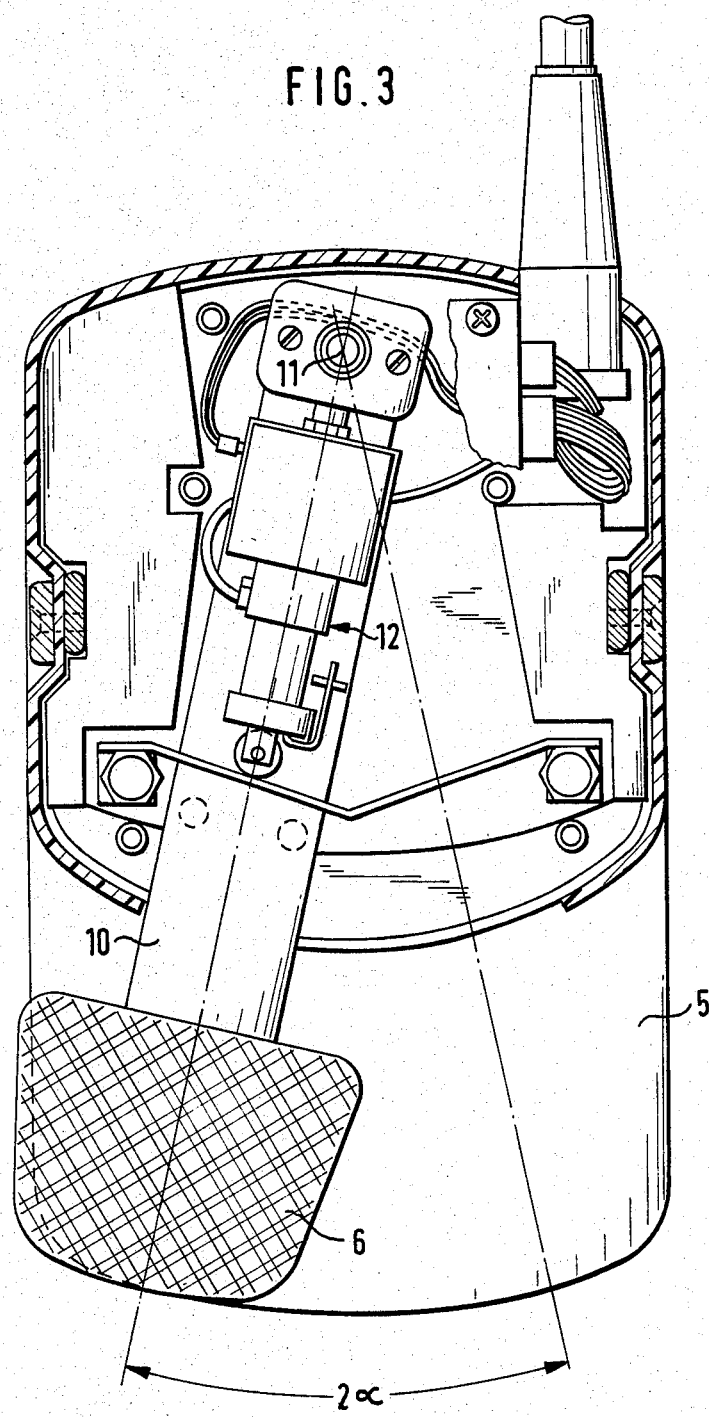
FIG. 3 illustrates the foot-actuated control arrangement of FIG. 2 in a another set position.

FIG. 3 illustrates the foot-actuated control arrangement which is shown in detail in FIG. 2, wherein the control element 12 is rendered ineffective, so that the actuating element is pivoted by means of its foot treadle 6 over the entire angle of 2 α between its end positions, without being automatically returned into a predetermined initial or basic position. Thereby, the applicable foot-actuated control arrangement can be utilized as a foot pedal starter in a dental treatment location, as is illustrated in FIG. 1. With reference to the details shown in FIG. 2, in the just previously mentioned mode of operation, the electromagnet is excited, and moreover, the pneumatic or hydraulic medium source is so operated that the compressed-air or hydraulic fluid contained within the cylinder 19 can be conveyed out of this cylinder 19 without any difficulty.

FIG. 4 illustrates the foot-actuated control arrangement of FIG. 2 in a longitudinal sectional view. Hereby, it can be ascertained that the base plate 5 supports the housing 30 which includes the opening 31 and which is connected with the carrying loop 3. In the right-hand of FIG. 4, a cylindrical bearing element 40 extends upwardly from the base plate 5 and forms the support location 11 according to FIG. 2. In the lower region of the support element 40, the latter will pivotably receive the actuating element or the actuating lever 10. A pressure spring 41 which contacts against a projection 42 on the bearing element 40 presses the actuating element 10 downwardly towards the base plate 5. By means of the limiting elements or screws 49, 50 which are connected with the actuating element 10 in the region of the bearing element 40, provision is made that the actuating element or the actuating lever 10 will not be pressed against the base plate 5 through the pressure spring 41, but remain freely movable at a spacing therefrom. In its forward region, the actuating element or actuating lever 10 includes a contact element 51 which serves as a pivot point, as illustrated in FIG. 5, when the actuating element 10 is pressed down with its foot pedal 6. During the course of such a movement, a pressure element 44 which is connected with the actuated element or actuating lever 10, and which is subjected to pressure by a spring 43, is pressed upwardly; in effect, away from the base plate 5. With the aid of the pressure element 44 there can thus be effectuated a control or switching function. Serving this purpose, for example, can be a pressure transducer 45 which is arranged opposite the pressure element 44 on a circuit board 35 which, at a spacing is fixed connected to the base plate 5. At this point it is noted that the previously mentioned movement of the actuating element or actuating lever 10 is possible in every pivoted position about the bearing element 40.

The previously described arrangement of the pressure element 44 is clearly ascertainable from the partially sectioned view according to FIG. 6. As illustrated therein, the pressure element 44 is received by a support plate 46 which is connected through spacer retainers 47, 48 with the actuating element or actuating lever 10.

In addition to the previously mentioned pressure transducer 45, the circuit board 35 on which there are arranged the required circuit component which can be interconnected with each other, can have two further pressure transducers connected therewith. Pressure transducers of that type, for instance, can be associated with the pushbuttons 7 and 8 of the foot-actuated control arrangement represented in FIG. 1. Illustrated in FIGS. 4 and 5 is a pressure transducer 46 of that type which may arranged opposite the bearing location 18 of the foot-actuated control arrangement, and which should be actuatable by means of the pushbutton 7. The pushbutton 7 is therefor associated with an actuating component 32 having a protrusion 34 which, upon the respective actuation of the pushbutton 7 (referring to FIG. 5) will in conjunction with the bearing location 18 act as a pressure element against the pressure transducer 46. The actuating component 32 is pivotably retained by means of a thin support plate 33 on the upper surface of the housing 30. A pressure spring 36 ensures that the applicable support plate 33, presses away upwardly relative to the base plate 5; in essence, will be pressed towards the upper surface of the housing.

Besides the previously considered elements, FIGS. 4 and 5 illustrate potentiometer 37 with its control element 38 previously referred to in conjunction with FIG. 2, which is can be adjusted through an actuating component 39 which, in the present instance, is connected with the setting control 12, and thereby with actuating element or actuating lever 10. The potentiometer 37 is a sliding potentiometer, as can be clearly ascertained from FIG. 7, in which the detail indicated by "X" in FIG. 5 is shown in a front elevational view on an enlarged scale. Thereby, from FIG. 7 it is clearly ascertainable that the control element 38 which is also designated as a slider of the potentiometer 37 which is fastened to the circuit board 35 can be varied when the actuating element or the actuating lever 10 and the therewith connected control element 12 are displaced; in essence; are pivoted, namely, about the bearing element 40. The potentiometer 37 is connected, for example, with a control circuit for a drive motor of a dental drill machine.

Through the foregoing there is described an embodiment of the foot-actuated control arrangement pursuant to the invention, in which with the control element 12 is so connected with the pivotable actuating element or actuating lever 10, that it becomes pivotable together with this actuating element or actuating lever 10. The capability of pivotal motion relates to a capability of pivoting about the bearing location 11 according to FIG. 2, and, respectively, the bearing element 40 according to FIGS. 4 and 6, as well as the capability of pivoting about the contact element 51. Hereby, there is indicated that the control element 12 is selectively activatable or deactivatable relative to the V-shaped guide track 17.

The configuration of the control element 12 in the type and mode disclosed in conjunction with FIG. 2, is particularly advantageous with regard to controllability. However, it is also possible that as a control element there be utilized and arranged a purely pneumatic or purely hydraulic, or also an only electromagnetically operating control element in a as would be the control element 12. For the remainder, in lieu of the above-mentioned control element 12, there can also be utilized a linear motor which has a pressure element corresponding to the pressure piston 15 contacting against the V-shaped guide track. Finally, however, it is also possible to arrange corresponding pneumatic, hydraulic or electromagnetically operating devices on the base plate 5, and to permit these to act on the actuating element or the actuating lever 10 in such a manner that during the effectiveness of those types of arrangement, it will be always automatically returned into a predetermined basic or initial position when an initially exerted setting or displacement force is removed therefrom. Arrangements of the last-mentioned type can hereby be fastened, for example, at both sides of the actuating lever 10, on the base plate 5 and upon their periods of actuation serve through a differential control to provide that the actuating lever or the actuating element 10 be placed into the desired initial or basic position.

Finally, it is also noted that, in lieu of the above-referred to potentiometer 37 or in addition to this potentiometer, there can be provided switch elements which are controllable through the control element 12. In addition thereto, it is possible that in addition to the potentiometer 37 there be provided a further potentiometer which is actuated in the corresponding manner as is the potentiometer 37. The hereby contemplated two potentiometers can be connected with different evaluating or control circuits, which can be provided in conformance with the two different modes of operation of the inventive foot-actuated control arrangement.

What is claimed is:

1. In a foot-actuated control arrangement, in particular for dental apparatuses including foot-treadle means displaceable from an initial position towards both sides in one plane; an actuating element actuatable on a switching and control element wherein said actuating element is displaceable along a pivot path about a bearing location, and at least one control element having a first, active position wherein said control element urges said actuating element to an initial position thereof along the pivot path and automatically reconveys said actuating element into said initial position subsequent to a displacement from said initial position; the improvement comprising: said control element includes a second, inactive position wherein the actuating element moves along its pivot path independent of said control element and may be held in every position along the pivot path; and means connected to the control element to move the control element between its first and second positions.

2. Arrangement as claimed in claim 1, wherein said actuating element is displaceable about a bearing location in a plane extending transverse to the previously mentioned plane, and during the course of its displacement about the bearing of location effects actuation of a switch element.

3. Arrangement as claimed in claim 1, wherein said actuating element includes a contact element supported on a guide track, and wherein said control element is constituted by said contact element.

4. Arrangement as claimed in claim 1, wherein said control element includes a fluid actuatable piston arrangement interconnected with said actuating element.

5. Arrangement as claimed in claim 1, wherein said control element comprises an electromagnetic arrangement interconnected with said actuating element.

6. Arrangement as claimed in claim 1, wherein said control element comprises a linear motor interconnected with the actuating element.

7. In a foot-actuated control arrangement, in particular for dental apparatuses including foot-treadle means displaceable from an initial position towards both sides in one plane; an actuating element actuatable on a switching and control element wherein said actuating element is displaceable along a pivot path about a bearing location, and at least one control element for maintaining said actuating element in the initial position thereof along the pivot path and for automatically reconveying said actuating element into said position subsequent to a displacement from said initial position; the improvement comprising in that said control element is settable into a non-returning condition upon the supply or disappearance of a separate control signal from its condition of automatic return, whereby the actuating element can remain in every possible set position along the pivot path; and in that said control element includes a running element arranged opposite and supported on a V-shaped guide track having its dividing point facing away from the running element, said guide track having both ends thereof fixed relative to the bearing location for the actuating element.

8. Arrangement as claimed in claim 7, wherein said running element comprises a roller at the end facing towards the V-shaped guide track.

9. In a foot-actuated control arrangement, in particular for dental apparatuses including foot-treadle means displaceable from an initial position towards both sides in one plane; an actuating element actuatable on a switching and control element wherein said actuating element is displaceable along a pivot path about a bearing location, and at least one control element for maintaining said actuating element in the initial position thereof along the pivot path and for automatically reconveying said actuating element into said position subsequent to a displacement from said initial position; the improvement comprising in that said control element is settable into a non-returning condition upon the supply or disappearance of a separate control signal from its condition of automatic return, whereby the actuating element can remain in every possible set position along the pivot path; in that said control element includes a fluid actuatable piston arrangement interconnected with said actuating element; and in that an electromagnet is provided for controlling the opening and closing of the fluid circuit of the piston arrangement.

* * * * *